United States Patent
Nicou et al.

(10) Patent No.: US 12,226,502 B2
(45) Date of Patent: Feb. 18, 2025

(54) DYEING COMPOSITION COMPRISING A SPECIFIC ANTHRAQUINONE CATIONIC DIRECT DYE, A CATIONIC SURFACTANT, AN AMPHOTERIC OR ZWITTERIONIC SURFACTANT AND A FATTY ALCOHOL

(71) Applicant: L'Oreal, Paris (FR)

(72) Inventors: Valérie Nicou, Saint-Ouen (FR); Samira Rharbi, Saint-Ouen (FR); Julie Blanc, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 18/013,790

(22) PCT Filed: Jun. 29, 2021

(86) PCT No.: PCT/EP2021/067825
§ 371 (c)(1),
(2) Date: Dec. 29, 2022

(87) PCT Pub. No.: WO2022/002923
PCT Pub. Date: Jan. 6, 2022

(65) Prior Publication Data
US 2023/0240955 A1    Aug. 3, 2023

(30) Foreign Application Priority Data
Jun. 30, 2020 (FR) ..................... 2006860

(51) Int. Cl.
*A61Q 5/10* (2006.01)
*A61K 8/34* (2006.01)
*A61K 8/35* (2006.01)
*A61K 8/73* (2006.01)
*A61K 8/89* (2006.01)
*A61Q 5/06* (2006.01)

(52) U.S. Cl.
CPC ............. *A61K 8/355* (2013.01); *A61K 8/342* (2013.01); *A61K 8/73* (2013.01); *A61K 8/89* (2013.01); *A61Q 5/065* (2013.01); *A61K 2800/432* (2013.01); *A61K 2800/596* (2013.01)

(58) Field of Classification Search
CPC .......... A61K 8/355; A61K 8/342; A61K 8/73; A61K 8/89; A61K 2800/432; A61K 2800/596; A61K 8/41; A61K 8/416; A61K 8/442; A61K 8/898; A61Q 5/065; A61Q 5/10

USPC ............................................. 8/405
See application file for complete search history.

(56) References Cited

U.S. PATENT DOCUMENTS

| | | | |
|---|---|---|---|
| 4,137,180 A | 1/1979 | Naik et al. | |
| 4,874,554 A | 10/1989 | Lange et al. | |
| 4,957,732 A | 9/1990 | Grollier et al. | |
| 6,437,149 B1 | 8/2002 | Genet et al. | |
| 9,442,366 B2* | 9/2016 | Tu | G03F 1/38 |
| 10,667,999 B2 | 6/2020 | Grosjacques et al. | |
| 2008/0313820 A1* | 12/2008 | Huet | A61K 8/73 8/429 |
| 2015/0257995 A1* | 9/2015 | Goutsis | A61K 8/355 8/405 |
| 2017/0273883 A1 | 9/2017 | Marsh et al. | |
| 2019/0038534 A1* | 2/2019 | Consoli | A61K 8/4926 |

FOREIGN PATENT DOCUMENTS

| | | | | |
|---|---|---|---|---|
| CA | 2613049 A1 * | 4/2008 | | A61Q 5/10 |
| DE | 102012221987 A1 * | 6/2014 | | A61Q 5/06 |
| EP | 0186507 A2 | 7/1986 | | |
| EP | 0342834 A2 | 11/1989 | | |
| FR | 2786484 A1 | 6/2000 | | |
| FR | 2883746 A1 | 10/2006 | | |
| WO | WO 2014082948 A2 * | 6/2014 | | A61Q 5/10 |
| WO | 2022/002920 A1 | 1/2022 | | |

OTHER PUBLICATIONS

STIC Search Report dated Apr. 4, 2024.*
International Search Report and Written Opinion for counterpart Application No. PCT/EP2021/067820, dated Sep. 20, 2021.
International Search Report and Written Opinion for counterpart Application No. PCT/EP2021/067825, dated Sep. 20, 2021.
Todd, Charles, et al., "Volatile Silicone Fluids for Cosmetic Formulations," Cosmetics and Toiletries, vol. 91, Jan. 1976, pp. 29-32.
Mintel: "Color Lustre," Shu Uemura Art of Hair, Record No. 1945697, XP055559785, Dec. 21, 2012.
Mintel: "Coloring Treatment," L'Oréal, Record No. 2890731, XP055559780, Jan. 12, 2015.

* cited by examiner

*Primary Examiner* — Eisa B Elhilo
(74) *Attorney, Agent, or Firm* — THE MARBURY LAW GROUP, PLLC

(57) ABSTRACT

The invention relates to a composition for dyeing human keratin fibers, preferably the hair, comprising: —one or more anthraquinone cationic direct dyes; —one or more polyols, —one or more anionic surfactants, and —one or more nonionic polysaccharides.

18 Claims, No Drawings

DYEING COMPOSITION COMPRISING A SPECIFIC ANTHRAQUINONE CATIONIC DIRECT DYE, A CATIONIC SURFACTANT, AN AMPHOTERIC OR ZWITTERIONIC SURFACTANT AND A FATTY ALCOHOL

CROSS REFERENCE TO RELATED APPLICATIONS

This is a National Stage Application of PCT/EP2021/067825, filed internationally on Jun. 29, 2021, which claims priority to French Application No. 2006860, filed on Jun. 30, 2020, the contents of both of which are incorporated by reference herein in their entireties.

One subject of the present invention is a composition for dyeing human keratin fibers, especially the hair, comprising at least one specific anthraquinone cationic direct dye, at least one cationic surfactant, at least one amphoteric or zwitterionic surfactant and at least one fatty alcohol. The invention also relates to a dyeing process using this composition.

Many people have sought for a long time to modify the color of their hair and in particular to mask their gray hair.

It is known practice to dye keratin fibers with dyeing compositions containing direct dyes. These compounds are colored and coloring molecules that have affinity for the fibers. It is known practice, for example, to use direct dyes of the nitrobenzene type, anthraquinone or nitropyridine dyes, and dyes of the azo, xanthene, acridine, azine or triarylmethane type.

These dyes are usually applied to fibers optionally in the presence of an oxidizing agent if it is desired to obtain simultaneous lightening of the fibers. Once the leave-on time has elapsed, the fibers are rinsed, optionally washed and dried.

The colorings resulting from the use of direct dyes are colorings that are often chromatic but are, however, only temporary or semi-permanent since the nature of the interactions that bind the direct dyes to the keratin fiber and their desorption from the surface and/or the core of the fiber are responsible for their weak dyeing power and their poor relative persistence with respect to washing or perspiration. Thus, the colorings may also not be sufficiently fast in the face of external agents such as light, shampoos and perspiration.

It is also difficult to obtain powerful and/or persistent colorings for certain shades, especially blue shades, in particular at acid pH values.

Furthermore, consumers are still in search of dye compositions that exhibit optimum usage qualities.

The objective of the present invention is to provide a dyeing composition which results in good dyeing properties and which exhibits improved usage qualities.

In particular, one of the objectives of the present invention is to provide direct dyeing compositions that make it possible to obtain a coloring with varied shades, especially shades that are natural, powerful, sparingly selective and that show good resistance to the various attacks to which the hair may be subjected, in particular shampoo washes.

Another objective of the present invention is to provide direct dyeing compositions which exhibit optimum usage qualities, and in particular which are applied easily and which are rinsed rapidly.

This objective is achieved by the present invention, one subject of which is especially a composition for dyeing keratin fibers such as the hair, comprising:

(a) one or more specific anthraquinone cationic direct dyes,
(b) one or more cationic surfactants,
(c) one or more amphoteric or zwitterionic surfactants, and
(d) one or more fatty alcohols.

By formulating these direct dyes of anthraquinone structure in this specific support, it is possible to obtain a composition that is easy to apply to the hair, without running, while having good dyeing properties. The composition obtained also makes it possible to obtain natural shades and a coloring that bleeds little, in particular after the final shampoo wash. They may therefore be rinsed rapidly, without using a large amount of water.

Another subject of the invention is a process for dyeing human keratin fibers, preferably the hair, characterized in that the composition is applied to the keratin fibers.

Other subjects, features, aspects and advantages of the invention will emerge even more clearly on reading the description and the examples that follow.

In the text hereinbelow, and unless otherwise indicated, the limits of a range of values are included in that range, notably in the expressions "between" and "ranging from . . . to . . . ".

Moreover, the expression "at least one" used in the present description is equivalent to the expression "one or more".

Specific Anthraquinone Cationic Direct Dye(s)

The composition according to the invention comprises at least one cationic direct dye of formula (I) below:

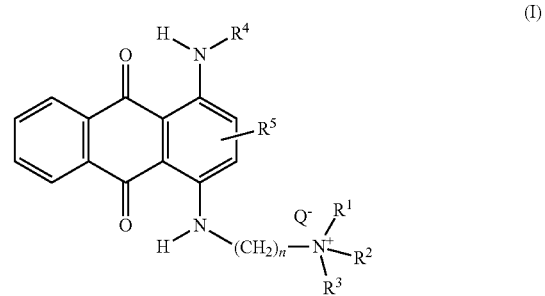

wherein:
  $R^1$, $R^2$ and $R^3$, which may be identical or different, representing a hydrogen atom or an optionally substituted ($C_1$-$C_8$)alkyl group;
  $R^4$ representing a hydrogen atom or an optionally substituted ($C_1$-$C_8$)alkyl group;
  $R^5$ representing a hydrogen atom, an optionally substituted ($C_1$-$C_8$)alkyl group, an optionally substituted ($C_1$-$C_8$)alkylene group, a halogen, a hydroxyl group or a ($C_1$-$C_8$)alkoxy group;
  n representing a number between 1 and 8;
  $Q^-$ represents an organic or mineral anionic counterion, such as a halide or an alkyl sulfate.
Preferably, in formula (I):
  $R^1$, $R^2$ and $R^3$, which may be identical or different, representing an optionally substituted ($C_1$-$C_6$)alkyl group;
  $R^4$ representing a hydrogen atom or optionally substituted ($C_1$-$C_6$)alkyl group;

R⁵ representing a hydrogen atom or an optionally substituted $(C_1-C_8)$alkyl group;

n representing a number between 1 and 6;

Q⁻ representing a halide or an alkyl sulfate.

More preferentially, in formula (I):

$R^1$, $R^2$ and $R^3$, which may be identical or different, representing an optionally substituted $(C_1-C_3)$alkyl group;

$R^4$ representing a hydrogen atom or a methyl, preferably a methyl;

$R^5$ representing a hydrogen atom or a methyl, preferably a hydrogen atom;

n representing a number between 2 and 4;

Q⁻ representing a halide or an alkyl sulfate, preferably a halide.

Among the dyes of formula (I), use may in particular be made of the dyes of formula (I') or of formula (I") below:

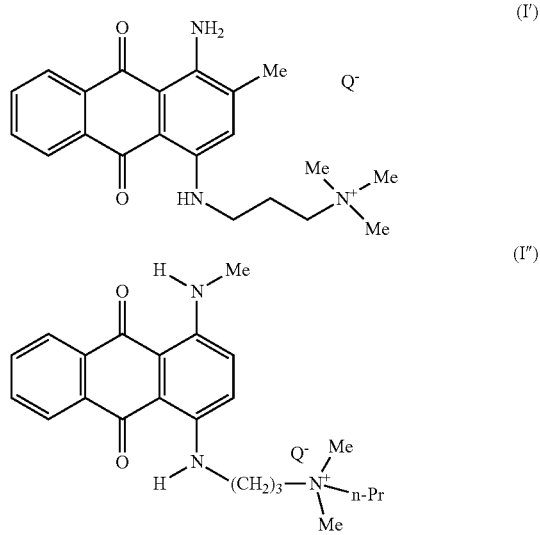

with Q⁻ being an anionic counterion, particularly a halide such as bromide or chloride, or an alkyl sulfate, such as methyl sulfate or mesityl. Preferably, Q⁻ is a halide, better still a bromide.

The term "anionic counterion" is intended to mean an anion or an anionic group derived from an organic or mineral acid salt which counterbalances the cationic charge of the dye; more particularly, the anionic counterion is chosen from: i) halides such as chloride or bromide; ii) nitrates; iii) sulfonates, including $C_1-C_6$ alkylsulfonates: Alk-S(O)$_2$O⁻ such as methanesulfonate or mesylate, and ethanesulfonate; iv) arylsulfonates: Ar—S(O)$_2$O⁻ such as benzenesulfonate and toluenesulfonate or tosylate; v) citrate; vi) succinate; vii) tartrate; viii) lactate; ix) alkyl sulfates: Alk-O—S(O)O⁻ such as methyl sulfate and ethyl sulfate; x) aryl sulfates: Ar—O—S(O)O⁻, such as benzene sulfate and toluene sulfate; xi) alkoxy sulfates: Alk S(O)$_2$O⁻ such as methoxy sulfate and ethoxy sulfate; xii) aryloxy sulfates: Ar—O—S(O)$_2$O⁻; xiii) phosphates O=P(OH)$_2$—O⁻, O=P(O⁻)$_2$—OH, O=P(O⁻)$_3$, HO—[P(O)(O⁻)]$_w$—P(O)(O⁻)$_2$ with w being an integer; xiv) acetate; xv) triflate; and xvi) borates such as tetrafluoroborate; xvii) disulfate (O=)$_2$S(O⁻)$_2$ or SO$_4^{2-}$ and monosulfate HSO$_4^-$.

One particularly preferred dye of formula (I') is HC Blue 17.

One particularly preferred dye of formula (I") is HC Blue 16 (1-methylamino-4-(3'-dimethylpropylammoniumpropylamino)antraquinone bromide).

Preferably, the cationic direct dye(s) of formula (I) is (are) chosen from the dyes of formula (I') and (I") and mixtures thereof, and preferentially from the dyes of formula (I").

Preferably, the cationic direct dye(s) of formula (I) is (are) chosen from HC Blue 16, HC Blue 17, or mixtures thereof, more preferentially HC Blue 16.

Advantageously, the total amount of cationic direct dye(s) of formula (I) varies from 0.01% to 15% by weight, preferably from 0.05% to 10% by weight, more preferentially from 0.1% to 5% by weight, better still from 0.3% to 3% by weight relative to the total weight of the composition.

Advantageously, the total amount of cationic direct dye(s) of formula (I") varies from 0.01% to 15% by weight, preferably from 0.05% to 10% by weight, more preferentially from 0.1% to 5% by weight, better still from 0.3% to 3% by weight relative to the total weight of the composition.

Cationic Surfactants

The cosmetic composition according to the present invention also comprises one or more cationic surfactants.

The term "cationic surfactant" is intended to mean a surfactant that is positively charged when it is contained in the composition according to the invention. This surfactant may bear one or more positive permanent charges or may contain one or more cationizable functions in the composition according to the invention.

The cationic surfactant(s) can be chosen from primary, secondary or tertiary fatty amines, which are optionally polyoxyalkylenated, or salts thereof, quaternary ammonium salts, and mixtures thereof. The cationic surfactant(s) are preferably chosen from quaternary ammonium salts.

The fatty amines generally comprise at least one $C_8-C_{30}$ hydrocarbon-based chain.

Examples of quaternary ammonium salts that may notably be mentioned include:

those corresponding to the following general formula (II):

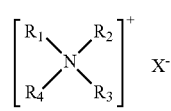

(II)

in which the groups $R_1$ to $R_4$, which may be identical or different, represent a linear or branched aliphatic group comprising from 1 to 30 carbon atoms, or an aromatic group such as aryl or alkylaryl, at least one of the groups $R_1$ to $R_4$ denoting a linear or branched aliphatic radical comprising from 8 to 30 carbon atoms, preferably from 12 to 24 carbon atoms. The aliphatic groups may include heteroatoms notably such as oxygen, nitrogen, sulfur and halogens. The aliphatic groups are chosen, for example, from $C_1-C_{30}$ alkyl, $C_1-C_{30}$ alkoxy, polyoxy$(C_2-C_6)$alkylene, $C_1-C_{30}$ alkylamide, $(C_{12}-C_{22})$alkylamido$(C_2-C_6)$alkyl, $(C_{12}-C_{22})$alkyl acetate and $C_1-C_{30}$ hydroxyalkyl groups; X⁻ is an anion chosen from the group of halides, phosphates, acetates, lactates, $(C_1-C_4)$alkyl sulfates and $(C_1-C_4)$alkylsulfonates or $(C_1-C_4)$alkylarylsulfonates.

Among the quaternary ammonium salts of formula (I), the ones that are preferred are, on the one hand, tetraalkylammonium salts, for instance dialkyldimethylammonium or alkyltrimethylammonium salts in which the alkyl group comprises approximately from 12 to 22 carbon atoms, in particular behenyltrimethylammonium, distearyldimethylammonium, cetyltrimethylammonium or benzyldimethylstearylammonium salts, or else, on the other hand, the palmitylamidopropyltrimethylammonium salts, the stearamidopropyltrimethylammonium salts, the stearamidopropyldimethylcetearylammonium salts, or the stearamidopropyldimethyl(myristyl acetate)ammonium salts sold under the name Ceraphyl® 70 by the company Van Dyk. It is preferred in particular to use the chloride salts of these compounds.

quaternary ammonium salts of imidazoline, such as, for example, those of formula (III) below:

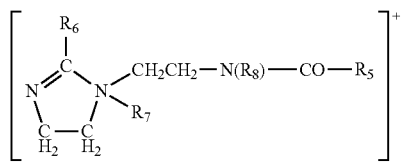
(III)

in which $R_5$ represents an alkenyl or alkyl group comprising from 8 to 30 carbon atoms, for example derived from tallow fatty acids, $R_6$ represents a hydrogen atom, a $C_1$-$C_4$ alkyl group or an alkenyl or alkyl group comprising from 8 to 30 carbon atoms, $R_7$ represents a $C_1$-$C_4$ alkyl group, $R_8$ represents a hydrogen atom or a $C_1$-$C_4$ alkyl group and $X^-$ is an anion chosen from the group of the halides, phosphates, acetates, lactates, alkyl sulfates, alkylsulfonates or alkylarylsulfonates, the alkyl and aryl groups of which preferably comprise, respectively, from 1 to 20 carbon atoms and from 6 to 30 carbon atoms. Preferably, $R_5$ and $R_6$ denote a mixture of alkenyl or alkyl groups including from 12 to 21 carbon atoms, for example derived from tallow fatty acids, $R_7$ denotes a methyl group and $R_8$ denotes a hydrogen atom. Such a product is sold, for example, under the name Rewoquat® W 75 by the company Rewo;

quaternary di- or triammonium salts in particular of formula (IV):

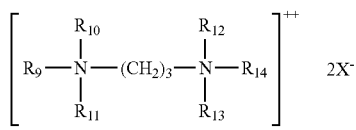
(IV)

in which $R_9$ denotes an alkyl radical comprising approximately from 16 to 30 carbon atoms, which is optionally hydroxylated and/or optionally interrupted with one or more oxygen atoms, $R_{10}$ is chosen from hydrogen or an alkyl radical comprising from 1 to 4 carbon atoms or a group $(R_{9a})(R_{10a})(R_{11a})N$—$(CH_2)_3$, $R_{9a}$, $R_{10a}$, $R_{11a}$, $R_{11}$, $R_{12}$, $R_{13}$ and $R_{14}$, which may be identical or different, are chosen from hydrogen or an alkyl radical comprising from 1 to 4 carbon atoms, and $X^-$ is an anion chosen from the group of halides, acetates, phosphates, nitrates, $(C_1$-$C_4)$alkyl sulfates, $(C_1$-$C_4)$alkyl sulfonates and $(C_1$-$C_4)$alkylaryl sulfonates, and in particular methyl sulfate and ethyl sulfate. Such compounds are, for example, Finquat CT-P, made available by the company Finetex (Quaternium 89), and Finquat CT, made available by the company Finetex (Quaternium 75), quaternary ammonium salts containing at least one ester function, such as those of formula (V) below:

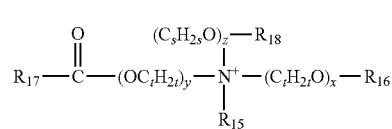
(V)

wherein:

$R_{15}$ is chosen from $C_1$-$C_6$ alkyl groups and $C_1$-$C_6$ hydroxyalkyl or dihydroxyalkyl groups;

$R_{16}$ is chosen from:

the group

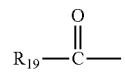

the groups $R_{20}$, which are linear or branched, saturated or unsaturated $C_1$-$C_{22}$ hydrocarbon-based groups, a hydrogen atom, $R_{18}$ is chosen from:

the group

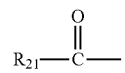

the groups $R_{22}$, which are linear or branched, saturated or unsaturated $C_1$-$C_6$ hydrocarbon-based groups, a hydrogen atom, $R_{17}$, $R_{19}$ and $R_{21}$, which may be identical or different, are chosen from linear or branched, saturated or unsaturated $C_7$-$C_{21}$ hydrocarbon-based groups;

r, s and t, which may be identical or different, are integers ranging from 2 to 6;

y is an integer ranging from 1 to 10;

x and z, which may be identical or different, are integers ranging from 0 to 10;

$X^-$ is a simple or complex, organic or mineral anion;

with the proviso that the sum x+y+z is from 1 to 15, that when x is 0 then $R_{16}$ denotes $R_{20}$, and that when z is 0 then $R_{18}$ denotes $R_{22}$.

The alkyl groups $R_{15}$ may be linear or branched, and more particularly linear.

Preferably, $R_{15}$ denotes a methyl, ethyl, hydroxyethyl or dihydroxypropyl group, and more particularly a methyl or ethyl group.

Advantageously, the sum x+y+z is from 1 to 10.

When $R_{16}$ is a hydrocarbon-based group $R_{20}$, it may be long and contain from 12 to 22 carbon atoms, or short and contain from 1 to 3 carbon atoms.

When $R_{18}$ is a hydrocarbon-based group $R_{22}$, it preferably contains 1 to 3 carbon atoms.

Advantageously, $R_{17}$, $R_{19}$ and $R_{21}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion that is compatible with the ammonium bearing an ester functional group.

The anion $X^-$ is even more particularly chloride or methyl sulfate.

Use may be made more particularly in the composition according to the invention of the ammonium salts of formula (V) in which:

$R_{15}$ denotes a methyl or ethyl group,
x and y are equal to 1;
z is equal to 0 or 1;
r, s and t are equal to 2;
$R_{16}$ is chosen from:
the group

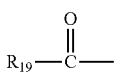

methyl, ethyl or $C_{14}$-$C_{22}$ hydrocarbon-based groups,
a hydrogen atom;
$R_{18}$ is chosen from:

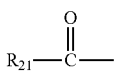

the group
a hydrogen atom;
$R_{17}$, $R_{19}$ and $R_{21}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Examples that may be mentioned include the compounds of formula (VI) such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are derived more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by a quaternization using an alkylating agent such as an alkyl halide (preferably a methyl or ethyl halide), a dialkyl sulfate (preferably a methyl or ethyl sulfate), methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in U.S. Pat. Nos. 4,874,554 and 4,137,180.

Use may be made of behenoylhydroxypropyltrimethylammonium chloride made available by KAO under the name Quatarmin BTC 131.

Preferably, the ammonium salts containing at least one ester function contain two ester functions.

Among the quaternary ammonium salts containing at least one ester function which may be used, it is preferred to use dipalmitoylethylhydroxyethylmethyl-ammonium salts.

The cationic surfactant(s) is (are) preferably chosen from those of formula (II) and those of formula (V) and even more preferentially from those of formula (II).

Most particularly preferably, the cationic surfactant(s) of the invention is (are) chosen from those of formula (II), more preferentially from behenyltrimethylammonium salts, cetyltrimethylammonium salts, and a mixture of these compounds, and even more preferentially from behenyltrimethylammonium chloride, cetyltrimethylammonium chloride, and a mixture of these compounds.

Preferably, the cationic surfactant(s) is (are) present in a total content ranging from 0.1% to 15% by weight, more preferentially from 0.5% to 10% by weight, and even more preferentially from 1% to 8% by weight, even better still from 2% to 5% by weight, relative to the total weight of the composition.

Advantageously, the total amount of cationic surfactant(s) of formula (II) ranges from 0.1% to 15% by weight, more preferentially from 0.5% to 10% by weight, and more preferentially still from 1% to 8% by weight, even better still from 2% to 5% by weight, relative to the total weight of the composition.

Amphoteric or Zwitterionic Surfactants

The cosmetic composition according to the invention also comprises one or more amphoteric or zwitterionic surfactants.

The amphoteric surfactants capable of being used in the invention can be optionally quaternized secondary or tertiary aliphatic amine derivatives, in which the aliphatic group is a linear or branched chain comprising from 8 to 22 carbon atoms, said amine derivatives containing at least one anionic group, such as, for example, a carboxylate, sulfonate, sulfate, phosphate or phosphonate group.

Mention may in particular be made of ($C_8$-$C_{20}$)alkyl betaines, sulfobetaines, ($C_8$-$C_{20}$)alkyl sulfobetaines, ($C_8$-$C_{20}$)alkylamido($C_1$-$C_6$)alkyl betaines, such as cocoamidopropyl betaine, ($C_8$-$C_{20}$)alkylamido($C_1$-$C_6$)alkyl sulfobetaines, and also mixtures thereof.

Mention may also be made, among the derivatives of optionally quaternized secondary or tertiary aliphatic amines capable of being employed, of the products with the following respective structures (A1) and (A2):

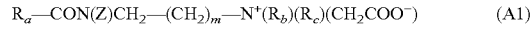

$R_a$—CON(Z)CH$_2$—(CH$_2$)$_m$—N$^+$(R$_b$)(R$_c$)(CH$_2$COO$^-$)     (A1)

wherein:
$R_a$ represents a $C_{10}$-$C_{30}$ alkyl or alkenyl group derived from an acid $R_a$—COOH preferably present in hydrolysed coconut oil, or a heptyl, nonyl or undecyl group,
$R_b$ represents a β-hydroxyethyl group,
$R_c$ represents a carboxymethyl group,
m is equal to 0, 1 or 2, and
Z represents a hydrogen atom or a hydroxyethyl or carboxymethyl group;

$$R_{a'}—CON(Z)CH_2—(CH_2)_m—N(B)(B') \quad (A2)$$

wherein:
B represents —$CH_2CH_2OX'$, with X' representing —$CH_2$—COOH, $CH_2$—COOZ', —$CH_2CH_2$—COOH, —$CH_2CH_2$—COOZ', or a hydrogen atom,
B' represents —$(CH_2)_z$—Y', with z=1 or 2, and Y' representing —COOH, —COOZ', —$CH_2$—CHOH—$SO_3H$ or $CH_2$—CHOH—$SO_3Z'$,
m' is equal to 0, 1 or 2,
Z represents a hydrogen atom or a hydroxyethyl or carboxymethyl group,
Z' represents an ion resulting from an alkali metal or alkaline earth metal, such as sodium, potassium or magnesium; an ammonium ion; or an ion resulting from an organic amine and in particular from an amino alcohol, such as monoethanolamine, diethanolamine or triethanolamine, monoisopropanolamine, diisopropanolamine or triisopropanolamine, 2-amino-2-methyl-1-propanol, 2-amino-2-methyl-1,3-propanediol and tris(hydroxymethyl) aminomethane, and
$R_{a'}$ represents a $C_{10}$-$C_{30}$ alkyl or alkenyl group of an acid $R_a$COOH preferably present in hydrolysed linseed oil or coconut oil, an alkyl group, in particular a $C_{17}$ alkyl group, and its iso form, or an unsaturated $C_{17}$ group.

The compounds corresponding to the formula (A2) are particularly preferred.

Among the compounds of formula (A2) for which X' represents a hydrogen atom, mention may be made of the compounds known under the (CTFA) names sodium cocoamphoacetate, sodium lauroamphoacetate, sodium caproamphoacetate and sodium capryloamphoacetate.

Other compounds of formula (A2) are known under the (CTFA) names disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

Mention may be made, as examples of compounds of formula (A2), of the cocoamphodiacetate sold by Rhodia under the trade name Miranol® $C_2M$ Concentrate, the sodium cocoamphoacetate sold under the trade name Miranol Ultra C 32 and the product sold by Chimex under the trade name Chimexane HA.

Use may also be made of the compounds of formula (A3):

$$R_{a''}—NH—CH(Y'')—(CH_2)_n—C(O)—NH—(CH_2)_{n'}—N(R_d)(R_e) \quad (A3)$$

wherein:
$R_{a''}$ represents a $C_{10}$-$C_{30}$ alkyl or alkenyl group of an acid;
$R_{a''}$—C(O)OH, preferably present in hydrolysed linseed oil or coconut oil;

Y" represents the —C(O)OH, —C(O)OZ" or —$CH_2$—CH(OH)—$SO_3H$ group or the $CH_2$—CH(OH)—$SO_3$—Z" group, with Z" representing a cation resulting from an alkali metal or alkaline earth metal, such as sodium, an ammonium ion or an ion resulting from an organic amine;
$R_d$ and $R_e$, independently of each other, represent a $C_1$-$C_4$ alkyl or hydroxyalkyl radical; and
n and n', independently of each other, denote an integer ranging from 1 to 3.

Among the compounds of formula (A3), mention may in particular be made of the compound classified in the CTFA dictionary under the name sodium diethylaminopropyl cocoaspartamide and notably the compound sold by the company Chimex under the name Chimexane HB.

The amphoteric or zwitterionic surfactant(s) are advantageously chosen from ($C_8$-$C_{20}$)alkylbetaines, ($C_8$-$C_{20}$)alkylamido($C_3$-$C_8$)alkylbetaines, and mixtures thereof, and preferably from cocoylbetaine and cocamidopropylbetaine, and mixtures thereof.

The total content of the amphoteric or zwitterionic surfactant(s) advantageously ranges from 0.1% to 20% by weight, preferably from 1% to 15% by weight, more preferentially from 2% to 10% by weight, relative to the total weight of the composition.

Advantageously, the total amount of amphoteric or zwitterionic surfactant(s) chosen from ($C_8$-$C_{20}$)alkyl betaines and ($C_8$-$C_{20}$)alkylamido($C_3$-$C_8$)alkyl betaines, and mixtures thereof, ranges from 0.1% to 20% by weight, preferably from 1% to 15% by weight, more preferentially from 2% to 10% by weight, relative to the total weight of the composition.

Fatty Alcohols

The composition according to the invention also comprises one or more fatty alcohols.

The term "fatty alcohol" means a long-chain aliphatic alcohol comprising from 8 to 40 carbon atoms and comprising at least one hydroxyl group OH. The fatty alcohols according to the invention are non-oxyalkylenated and non-glycerolated.

The fatty alcohols according to the invention may be saturated or unsaturated, and linear or branched, and comprise from 8 to 40 carbon atoms.

More preferentially, the fatty alcohols according to the invention are chosen from compounds having the structure R—OH with R denoting a linear or branched, saturated or unsaturated alkyl group optionally substituted with one or more hydroxyl groups, comprising from 8 to 40, better still from 10 to 30, or even from 12 to 24 and even better still from 14 to 22 carbon atoms.

The fatty alcohols may be chosen from solid fatty alcohols and liquid fatty alcohols, and mixtures thereof.

For the purposes of the present invention, the term "solid fatty alcohol" means a fatty alcohol with a melting point of greater than 25° C., preferably greater than or equal to 28° C., more preferentially greater than or equal to 30° C. at atmospheric pressure (1.013×10⁵ Pa).

The solid fatty alcohols may be chosen from saturated or unsaturated, linear or branched solid fatty alcohols, comprising from 8 to 40 carbon atoms.

The solid fatty alcohols that may be used according to the invention are preferably chosen from compounds having the structure R—OH with R denoting a saturated linear alkyl group, optionally substituted with one or more hydroxyl groups, comprising from 8 to 40, better still from 10 to 30, or even from 12 to 24 and even better still from 14 to 22 carbon atoms.

The solid fatty alcohols that may be used may be chosen, alone or as a mixture, from:
lauryl alcohol (or 1-dodecanol);
myristyl alcohol (or 1-tetradecanol);
cetyl alcohol (or 1-hexadecanol);
stearyl alcohol (or 1-octadecanol);
arachidyl alcohol (or 1-eicosanol);
behenyl alcohol (or 1-docosanol);
lignoceryl alcohol (or 1-tetracosanol);
ceryl alcohol (or 1-hexacosanol);
montanyl alcohol (or 1-octacosanol);
myricyl alcohol (or 1-triacontanol).

For the purposes of the present invention, the term "liquid fatty alcohol" means a fatty alcohol with a melting point of less than or equal to 25° C., preferably less than or equal to 20° C. at atmospheric pressure ($1.013 \times 10^5$ Pa).

The liquid fatty alcohols that may be used according to the invention are preferably chosen from compounds having the structure R—OH with R denoting a saturated or unsaturated, linear or branched, preferably unsaturated and/or branched, alkyl group optionally substituted with one or more hydroxyl groups, comprising from 8 to 40, better still from 10 to 30, or even from 12 to 24 and even better still from 14 to 22 carbon atoms.

The liquid fatty alcohols that may be used may be chosen, alone or as a mixture, from oleyl alcohol, linoleyl alcohol, linolenyl alcohol, isocetyl alcohol, isostearyl alcohol, 2-octyl-1-dodecanol, 2-butyloctanol, 2-hexyl-1-decanol, 2-decyl tetradecanol and 2-tetradecyl-1-cetanol, and mixtures thereof.

Preferably, the $C_8$ to $C_{40}$ fatty alcohol(s) is (are) chosen from solid $C_8$ to $C_{40}$ fatty alcohols.

More particularly preferably, the $C_8$-$C_{40}$ fatty alcohols are chosen from solid $C_8$ to $C_{40}$ fatty alcohols comprising a saturated linear alkyl group, comprising from 8 to 40, better still from 10 to 30, or even from 12 to 24, even better still from 14 to 22 carbon atoms, better still from cetyl alcohol, stearyl alcohol and mixtures thereof.

Advantageously, the $C_8$ to $C_{40}$ fatty alcohol(s) are present in a total content ranging from 1% to 20% by weight, preferably from 2% to 15% by weight, better still from 4% to 10% by weight, relative to the total weight of the composition.

Advantageously, the solid $C_8$ to $C_{40}$ fatty alcohol(s) comprising a saturated linear alkyl group are present in a total content ranging from 1% to 20% by weight, preferably from 2% to 15% by weight, better still from 4% to 10% by weight, relative to the total weight of the composition.

Polysaccharide

The composition according to the invention may optionally comprise one or more polysaccharides.

For the purposes of the present invention, the term "polysaccharides" refers to a polymer constituted of sugar units.

For the purposes of the present invention, the term "sugar unit" is intended to mean an oxygen-comprising hydrocarbon-based compound which has several alcohol functions, with or without aldehyde or ketone function, and which comprises at least 4 carbon atoms.

The sugar units can be optionally modified by substitution, and/or by oxidation and/or by dehydration.

The sugar units that may be included in the composition of the polysaccharides of the invention are preferably derived from the following sugars: glucose, galactose, arabinose, rhamnose, mannose, xylose, fucose, anhydrogalactose, galacturonic acid, glucuronic acid, mannuronic acid, galactose sulfate, anhydrogalactose sulfate and fructose.

Preferably, the polysaccharides according to the invention are microbial polysaccharides, that is to say produced by bacteria or fungi.

Mention may most particularly be made, alone or as a mixture, of:
carrageenans (galactose polymers) and furcellerans (anhydrogalactose polymers);
xanthan gum (polymer of glucose, of mannose, of pyruvic acid and of glucuronic acid);
scleroglucan gum (glucose polymer);
gellan gum (polymer of partially acylated glucose, rhamnose and glucuronic acid).

These polymers can be physically or chemically modified. As physical treatment, mention may notably be made of a heat treatment. Chemical treatments that may be mentioned include esterification, etherification, amidation and oxidation reactions. These treatments make it possible to produce polymers that may notably be nonionic, anionic or amphoteric.

Preferably, the polysaccharide(s) are chosen from anionic polysaccharides, nonionic polysaccharides, and mixtures thereof, preferentially from nonionic polysaccharides, and mixtures thereof.

More preferentially, the polysaccharide(s) are chosen from carrageenans and furcellerans, xanthan gum, gellan gum, scleroglucan gum, and mixtures thereof.

Particularly preferably, the polysaccharide is scleroglucan gum.

The polysaccharides may also be chosen from modified or unmodified starches, guar gums and derivatives thereof, celluloses and derivatives thereof and in particular hydroxyethylcelluloses.

Advantageously, the total content of the polysaccharide(s), when they are present, ranges from 0.01% to 20% by weight, preferably from 0.05% to 10% by weight, more preferentially from 0.07% to 5% by weight, and more preferentially still from 0.1% to 3% by weight, relative to the total weight of the composition.

Advantageously, the total content of scleroglucan gum, when it is present, ranges from 0.01% to 20% by weight, preferably from 0.05% to 10% by weight, more preferentially from 0.07% to 5% by weight, and more preferentially still from 0.1% to 3% by weight, relative to the total weight of the composition.

Silicone

The composition according to the invention may also comprise one or more silicones, which may be solid or liquid, and volatile or non-volatile.

The silicones that may be used may be soluble or insoluble in the composition according to the invention; they may be in the form of oil, wax, resin or gum; silicone oils and gums are preferred.

Silicones are in particular described in detail in Walter Noll's *Chemistry and Technology of Silicones* (1968), Academic Press.

The volatile silicones may be chosen from those with a boiling point of between 60° C. and 260° C. (at atmospheric pressure) and more particularly from:
i) cyclic polydialkylsiloxanes comprising from 3 to 7 and preferably 4 to 5 silicon atoms, such as
octamethylcyclotetrasiloxane and decamethylcyclopentasiloxane.

Mention may be made of the products sold under the name Volatile Silicone 7207 by Union Carbide or Silbione 70045 V 2 by Rhodia, Volatile Silicone 7158 by Union Carbide or Silbione 70045 V 5 by Rhodia.

cyclocopolymers of the dimethylsiloxane/methylalkylsiloxane type having the chemical structure:

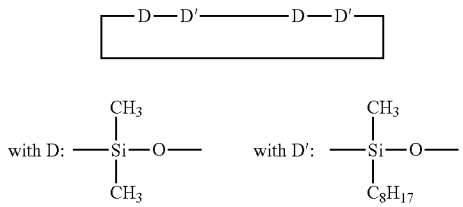

Mention may be made of Volatile Silicone FZ 3109 sold by the company Union Carbide;

mixtures of cyclic silicones with silicon-based organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

ii) linear polydialkylsiloxanes containing 2 to 9 silicon atoms, which generally have a viscosity of less than or equal to $5\times10^{-6}$ m$^2$/s at 25° C., such as decamethyltetrasiloxane.

Other silicones belonging to this category are described in the article published in Cosmetics and Toiletries, Vol. 91, January 76, pages 27-32, Todd & Byers *Volatile Silicone Fluids for Cosmetics*; mention may be made of the product sold under the name SH 200 by the company Toray Silicone.

Among the non-volatile silicones, mention may be made, alone or as a mixture, of polydialkylsiloxanes and in particular polydimethylsiloxanes (PDMS), polydiarylsiloxanes, polyalkylarylsiloxanes, silicone gums and resins, and also organopolysiloxanes (or organomodified polysiloxanes, or alternatively organomodified silicones) which are polysiloxanes including in their structure one or more organofunctional groups, generally attached via a hydrocarbon-based group, and preferably chosen from aryl groups, amine groups, alkoxy groups and polyoxyethylene or polyoxypropylene groups.

The organomodified silicones may be polydiarylsiloxanes, in particular polydiphenylsiloxanes, and polyalkylarylsiloxanes functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of organopolysiloxanes comprising:

polyoxyethylene and/or polyoxypropylene groups optionally including $C_6$-$C_{24}$ alkyl groups, such as dimethicone copolyols, and notably those sold by the company Dow Corning under the name DC 1248 or the oils Silwet® L 722, L 7500, L 77 and L 711 from the company Union Carbide; or alternatively $(C_{12})$alkylmethicone copolyols, and notably those sold by the company Dow Corning under the name Q2-5200;

substituted or unsubstituted amine groups, in particular $C_1$-$C_4$ aminoalkyl groups; mention may be made of the products sold under the names GP4 Silicone Fluid and GP7100 by the company Genesee, or under the names Q2-8220 and DC929 or DC939 by the company Dow Corning;

thiol groups, such as the products sold under the names GP 72 A and GP 71 from Genesee;

alkoxylated groups, such as the product sold under the name Silicone Copolymer F-755 by SWS Silicones and Abil Wax® 2428, 2434 and 2440 by the company Goldschmidt;

hydroxylated groups, for instance polyorganosiloxanes bearing a hydroxyalkyl function;

acyloxyalkyl groups, such as the polyorganosiloxanes described in U.S. Pat. No. 4,957,732;

anionic groups of the carboxylic acid type, as described, for example, in EP 186 507, or of the alkylcarboxylic type, such as the product X-22-3701E from the company Shin-Etsu; or else of the 2-hydroxyalkylsulfonate or 2-hydroxyalkylthiosulfate type, such as the products sold by the company Goldschmidt under the names Abil® S201 and Abil® S255;

hydroxyacylamino groups, such as the polyorganosiloxanes described in patent application EP 342 834; mention may be made, for example, of the product Q2-8413 from the company Dow Corning.

The silicones may also be chosen from polydialkylsiloxanes, among which mention may be made mainly of polydimethylsiloxanes bearing trimethylsilyl end groups. Among these polydialkylsiloxanes, mention may be made of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C1-C20)dialkylsiloxanes.

Products that may be used more particularly in accordance with the invention are mixtures such as:

mixtures formed from a polydimethylsiloxane with a hydroxy-terminated chain, or dimethiconol (CTFA), and from a cyclic polydimethylsiloxane, also known as cyclomethicone (CTFA), such as the product Q2-1401 sold by the company Dow Corning.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ m$^2$/s at 25° C.

Among these polyalkylarylsiloxanes, mention may be made of the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

The silicones with amino group(s) may be chosen from the amino silicones having the following general formula:

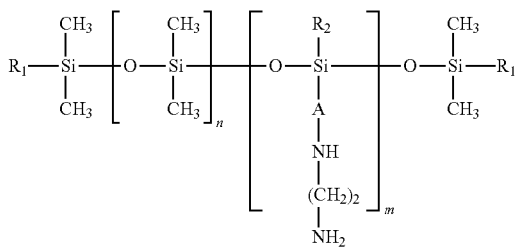

wherein:

A denotes a linear or branched C2-C8, preferably C3, alkylene radical.

R1 and R2 denote, independently of one another, a C1-C4 alkyl, preferably methyl, radical or a C1-C4 alkoxy, preferably methoxy, radical or a hydroxyl radical, m and n are numbers such that the weight-average molecular weight (Mw) is greater than or equal to 75 000.

A particularly preferred amino silicone is, for example, Dow Corning 2-8299® Cationic Emulsion from the company Dow Corning.

Preferably, the silicone(s) is (are) chosen from silicones comprising one or more amino groups.

The composition may comprise the silicones in an amount ranging from 0.01% to 30% by weight, preferably from 0.1% to 10% by weight and better still from 0.2% to 5% by weight, relative to the total weight of the composition.

In a preferred variant, the composition may comprise the amino silicones in an amount ranging from 0.01% to 30% by weight, preferably from 0.1% to 10% by weight and better still from 0.2% to 5% by weight, relative to the total weight of the composition.

Basifying Agents

The composition according to the invention may also comprise one or more basifying agents.

The basifying agent may be inorganic or organic or hybrid.

The inorganic basifying agent(s) is (are) preferably chosen from aqueous ammonia, alkali metal carbonates or bicarbonates, sodium hydroxide and potassium hydroxide, and mixtures thereof.

The organic basifying agent(s) is (are) preferably chosen from organic amines with a pKb at 25° C. of less than 12, preferably less than 10 and even more advantageously less than 6. It should be noted that this is the pKb corresponding to the function of highest basicity.

The organic basifying agent(s) is (are) chosen, for example, from alkanolamines, oxyethylenated and/or oxypropylenated ethylenediamines, amino acids and the compounds of formula (A1) below:

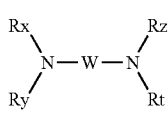

(A1)

wherein W is a $C_1$-$C_6$ alkylene residue optionally substituted with a hydroxyl group or a $C_1$-$C_6$ alkyl radical;

Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" is intended to mean an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for performing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and include at least one acid function chosen more particularly from carboxylic acid, sulfonic acid, phosphonic acid and phosphoric acid functions. The amino acids may be in neutral or ionic form.

As amino acids that can be used in the present invention, mention may in particular be made of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (A2) below:

(A2)

in which R denotes a group chosen from:

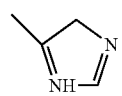

—(CH$_2$)$_3$NH$_2$

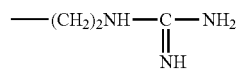

—(CH$_2$)$_2$NH$_2$
—(CH$_2$)$_2$NHCONH$_2$.

The compounds corresponding to formula (A2) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that can be used in the present invention, mention may notably be made of carnosine, anserine and balenine.

The organic amine may also be chosen from compounds comprising a guanidine function. As amines of this type that can be used in the present invention, besides arginine, which has already been mentioned as an amino acid, mention may notably be made of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl] amino)ethane-1-sulfonic acid.

Preferably, the organic amine present in the dyeing composition of the invention is an alkanolamine.

More preferentially still, the organic amine is 2-amino-2-methyl-1-propanol.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the composition according to the invention comprises an organic amine, preferably an alkanolamine, and more preferably 2-amino-2-methyl-1-propanol.

Advantageously, the total content of basifying agent(s) ranges from 0.01% to 10% by weight, preferably from 0.05% to 5% by weight and more preferably from 0.1% to 2% relative to the total weight of the composition.

In one particular embodiment, the total content of organic amine(s) ranges from 0.01% to 10% by weight, preferably from 0.05% to 5% by weight and more preferably from 0.1% to 2% relative to the total weight of the composition.

Polyol

The composition according to the invention may also comprise one or more polyols.

For the purposes of the present invention, the term "polyol" means an organic compound constituted of a hydrocarbon-based chain optionally interrupted with one or more oxygen atoms and bearing at least two free hydroxyl groups (—OH) borne by different carbon atoms, this compound possibly being cyclic or acyclic, linear or branched, and saturated or unsaturated.

More particularly, the polyol(s) that may be used according to the invention comprise from 2 to 30 hydroxyl groups, more preferentially from 2 to 10 hydroxyl groups and even more preferentially from 2 to 3 hydroxyl groups.

The polyol(s) that may be used according to the invention generally comprise at least two carbon atoms.

Preferably, said polyol(s) that may be used according to the invention are chosen from polyols comprising at least three carbon atoms, and are preferably chosen from propylene glycol, 1,3-propanediol, 1,3-butylene glycol, 1,2-pentanediol, dipropylene glycol, hexylene glycol, pentylene glycol, glycerol and ethylene glycol, and a mixture of these compounds.

Most particularly preferably, said polyol(s) that may be used according to the invention are chosen from propylene glycol, hexylene glycol, glycerol and a mixture of these compounds.

Preferably, the polyol(s) are present in the composition in a total content ranging from 0.01% to 20% by weight, 0.1-15% preferably from 0.5% to 12% by weight, more preferentially from 1% to 10% by weight, and better still from 2% to 8% by weight, relative to the total weight of the composition.

The composition according to the invention is preferably aqueous. When it is aqueous, the composition according to the invention comprises water in a content preferably ranging from 20% to 98% by weight, better still from 50% to 95% by weight and even better still from 70% to 90% by weight, relative to the total weight thereof.

The pH of the composition is preferably less than or equal to 8. The pH may range from 5 to 8 and preferably from 5 to 7.

Additives

The composition according to the present invention may also optionally comprise one or more additives, different from the compounds of the invention and among which mention may be made of nonionic or anionic surfactants, nonionic, cationic, anionic or amphoteric polymers or mixtures thereof other than polysaccharides, antidandruff agents, anti-seborrhoea agents, vitamins and provitamins including panthenol, sunscreens, mineral or organic pigments, sequestrants, plasticizers, solubilizers, acidifying agents, opacifiers or pearlescent agents, antioxidants, hydroxy acids, fragrances, preserving agents and pigments.

Of course, those skilled in the art will take care to choose this or these optional additional compounds so that the advantageous properties intrinsically associated with the composition according to the invention are not, or not substantially, detrimentally affected by the envisioned addition(s).

The above additives may generally be present in an amount, for each of them, of between 0 and 20% by weight, relative to the total weight of the composition.

The examples that follow serve to illustrate the invention without, however, being limiting in nature.

EXAMPLES

In the examples that follow, all the amounts are given as weight percentages of active material (AM) relative to the total weight of the composition, unless otherwise specified.

Example 1

Compositions A and B were prepared from the ingredients whose contents are indicated in the table below:

TABLE 1

| | A | B (comparative) |
|---|---|---|
| CETEARYL ALCOHOL | 7 | 7 |
| PROPYLENE GLYCOL | 2 | 2 |
| XIAMETER MEM-8299 EMULSION | 1.8 (raw material) | 1.8 (raw material) |
| AMODIMETHICONE | 1.03 | 1.03 |
| TRIDECETH-6 | 0.09 | 0.09 |
| CETRIMONIUM CHLORIDE | 0.018 | 0.018 |
| SCLEROTIUM GUM | 1 | 1 |
| ETHANOLAMINE | 0.04 | 0.04 |
| COCAMIDOPROPYL BETAINE | 3.8 | — |
| BEHENTRIMONIUM CHLORIDE | 3.16 | 6.96 |
| HC BLUE NO. 16 | 1 | 1 |
| Preserving agent | 0.74 | 0.74 |
| Water | qs 100 | qs 100 |
| pH | 6.7 ± 0.3 | 6.7 ± 0.3 |

Measurement of the Viscosity of the Compositions:

The viscosity is measured by means of a Rheomat RM 180 rheometer (200 rpm, 21.9° C., measurement at 30 s, spindle 3).

The results obtained are as follows (expressed in mPa·s):

TABLE 2

|  | Composition A | Composition B |
| --- | --- | --- |
| Viscosity | 815 mPa · s | 1060 mPa · s |

Composition A according to the invention has a lower viscosity than comparative composition B. Thus, composition A according to the invention is easy to use, that is to say easy to apply and to spread uniformly on the hair.

Dyeing Results:

Compositions A and B are applied to locks of natural 90% gray hair, in a proportion of 5 g of composition per gram of lock of hair.

The locks were then placed on hotplates thermostatically regulated at 27° C. After a leave-on time of 15 minutes, the locks are rinsed and dried.

The coloration of the locks of hair is evaluated in the L*a*b* system, with a MINOLTA CM2002 ® spectrophotometer.

In this system, L* represents the intensity; the lower the value of L*, the more intense and powerful the coloring.

TABLE 3

|  | L* |
| --- | --- |
| A (invention) | 35.32 |
| B (comparative) | 37.94 |

A more powerful coloring of the locks is obtained with composition A according to the invention than with composition B.

Study of the Color of the Rinsing Water (Bleeding Test) after One Shampoo Wash:

Compositions A and B were applied to locks of natural gray hair in a proportion of 5 g of composition per gram of hair. At the end of a leave-on time of 15 min, the hair is rinsed and then washed with a standard shampoo. It is observed that the color of the rinsing water for the locks dyed with composition A is lighter than that of the locks dyed with composition B: there is less bleeding of the color with composition A according to the invention compared to composition B.

Example 2

Compositions A1 and B1 were prepared from the ingredients whose contents are indicated in the table below:

TABLE 4

|  | A1 invention | B1 comparative |
| --- | --- | --- |
| PROPYLENE GLYCOL | 2 | 2 |
| AMODIMETHICONE | 1 | 1 |
| SCLEROTIUM GUM | 1 | 1 |
| ETHANOLAMINE | 0.04 | 0.04 |
| DISODIUM COCOAMPHODIACETATE | 3.8 | 3.8 |
| DIPALMITOYLETHYL HYDROXYETHYLMONIUM METHOSULFATE | 3.16 | — |
| CETEARYL ALCOHOL | 7.37 | 7.37 |
| HC BLUE NO. 16 | 1 | 1 |
| Preservative | 0.74 | 0.74 |
| Water | Qs 100 | Qs 100 |
| pH | 6.7 +/− 0.3 | 6.7 +/− 0.3 |

Dyeing Results:

Compositions A1 and B1 are applied to locks of permed wave white hair, in a proportion of 5 g of composition per gram of lock of hair.

The locks were then placed on hotplates thermostatically regulated at 27° C. After a leave-on time of 15 minutes, the locks are rinsed and dried.

The coloration of the locks of hair is evaluated in the L*a*b* system, with a MINOLTA CM2002 ® spectrophotometer.

In this system, L* represents the intensity; the lower the value of L*, the more intense and powerful the coloring.

TABLE 5

|  | L* |
| --- | --- |
| A (invention) | 33.76 |
| B (comparative) | 37.61 |

A more powerful coloring of the locks is obtained with composition A1 according to the invention than with composition B1.

Study of the Color of the Rinsing Water (Bleeding Test) after One Shampoo Wash:

Compositions A1 and B1 were applied to locks of hair in a proportion of 5 g of composition per gram of hair. At the end of a leave-on time of 15 min, the hair is rinsed and then washed with a standard shampoo. It is observed that the color of the rinsing water for the locks dyed with composition A1 is lighter than that of the locks dyed with composition B1: there is less bleeding of the color with composition A1 according to the invention compared to composition B1.

The invention claimed is:

1. A composition for dyeing keratin fibers, comprising:
(a) at least one cationic direct dye of formula (I):

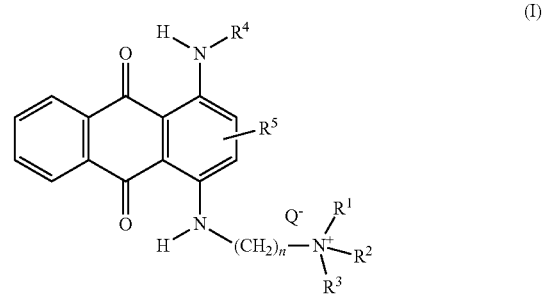

wherein:
R$^1$, R$^2$ and R$^3$ are independently chosen from a hydrogen atom or an optionally substituted (C$_1$-C$_8$) alkyl group;
R$^4$ represents a hydrogen atom or an optionally substituted (C$_1$-C$_5$) alkyl group;

R⁵ represents a hydrogen atom, an optionally substituted ($C_1$-$C_8$) alkyl group, an optionally substituted ($C_1$-$C_8$) alkylene group, a halogen, a hydroxyl group, or a ($C_1$-$C_8$) alkoxy group;

n represents a number between 1 and 8; and $Q^-$ represents an organic or mineral anionic counterion, (b) at least one cationic surfactant, wherein the total amount of cationic surfactants ranges from 0.1% to 15%, (c) at least one amphoteric or zwitterionic surfactant, where the total amount of amphoteric and zwitterionic surfactants ranges from 0.1% to 20%, and (d) at least one fatty alcohol, wherein all amounts are by weight, relative to the total weight of the composition.

2. The composition of claim 1, comprising at least one cationic direct dye chosen from cationic dyes of formula (I') or (I"):

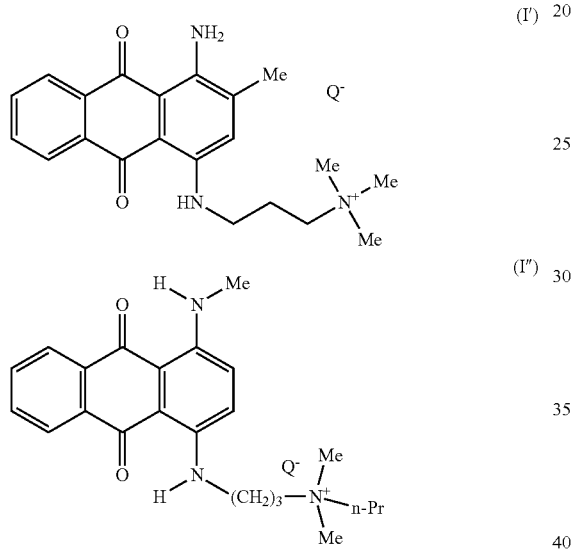

wherein $Q^-$ represents an anionic counterion.

3. The composition of claim 1, comprising at least one cationic direct dye chosen from HC Blue 16 or HC Blue 17.

4. The composition of claim 1, wherein the total amount of cationic direct dyes of formula (I) ranges from 0.01% to 15% by weight, relative to the total weight of the composition.

5. The composition of claim 1, comprising at least one cationic surfactant (b) chosen from:

cationic surfactants corresponding to the general formula (II):

wherein:
the groups $R_1$ to $R_4$ are independently chosen from a linear or branched aliphatic group comprising from 1 to 30 carbon atoms, or an aromatic group, wherein at least one of the groups $R_1$ to $R_4$ represents a linear or branched aliphatic radical comprising from 8 to 30 carbon atoms, and $X^-$ is an anion chosen from halides, phosphates, acetates, lactates, ($C_1$-$C_4$) alkyl sulfates, ($C_1$-$C_4$) alkylsulfonates, or ($C_1$-$C_4$) alkylarylsulfonates, quaternary ammonium salts of imidazoline of formula (III):

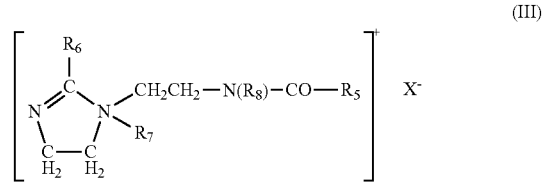

wherein:
$R_5$ represents an alkenyl or alkyl group comprising from 8 to 30 carbon atoms, $R_6$ represents a hydrogen atom, a $C_1$-$C_4$ alkyl group, or an alkenyl or alkyl group comprising from 8 to 30 carbon atoms, $R_7$ represents a $C_1$-$C_4$ alkyl group, $R_8$ represents a hydrogen atom or a $C_1$-$C_4$ alkyl group, and $X^-$ is an anion chosen from halides, phosphates, acetates, lactates, alkyl sulfates, alkylsulfonates or alkylarylsulfonates in which the alkyl and aryl groups comprise, respectively, from 1 to 20 carbon atoms and from 6 to 30 carbon atoms, quaternary diammonium or triammonium salts of formula (IV):

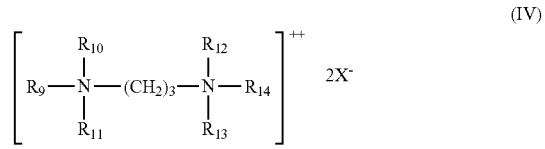

wherein:
$R_9$ denotes an alkyl radical comprising from 16 to 30 carbon atoms, which is optionally hydroxylated and/or optionally interrupted with one or more oxygen atoms, $R_{10}$ is chosen from hydrogen or an alkyl radical comprising from 1 to 4 carbon atoms or a group ($R_{9a}$)($R_{10a}$)($R_{11a}$)N—(CH$_2$)$_3$, $R_{9a}$, $R_{10a}$, $R_{11a}$, $R_{11}$, $R_{12}$, $R_{13}$ and $R_{14}$, which may be identical or different, are chosen from hydrogen or an alkyl radical comprising from 1 to 4 carbon atoms, and $X^-$ is an anion chosen from halides, acetates, phosphates, nitrates, ($C_1$-$C_4$) alkyl sulfates, ($C_1$-$C_4$) alkylsulfonates, and ($C_1$-$C_4$) alkylarylsulfonates, or quaternary ammonium salts of formula (V):

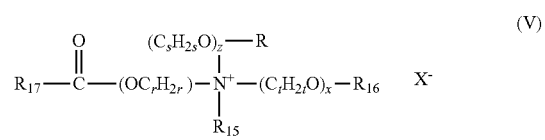

wherein:

$R_{15}$ is chosen from $C_1$-$C_6$ alkyl groups or $C_1$-$C_6$ hydroxyalkyl or dihydroxyalkyl groups, $R_{16}$ is chosen from:

the group:

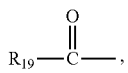

the groups $R_{20}$, which are linear or branched, saturated or unsaturated $C_1$-$C_{22}$ hydrocarbon-based groups, or a hydrogen atom, $R_{18}$ is chosen from:

the group:

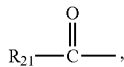

the groups $R_{22}$, which are linear or branched, saturated or unsaturated $C_1$-$C_6$ hydrocarbon-based groups, or a hydrogen atom, $R_{17}$, $R_{19}$ and $R_{21}$, which may be identical or different, are chosen from linear or branched, saturated or unsaturated $C_7$-$C_{21}$ hydrocarbon-based groups;

r, s, and t, which may be identical or different, are integers ranging from 2 to 6;

y is an integer ranging from 1 to 10;

x and z, which may be identical or different, are integers ranging from 0 to 10; and $X^-$ is a simple or complex and organic or mineral anion; with the provisos that:

the sum x+y+z is from 1 to 15, when x is 0 then $R_{16}$ denotes $R_{20}$, and when z is 0 then $R_{18}$ denotes $R_{22}$.

6. The composition of claim 5, comprising at least one cationic surfactant chosen from those of formula (II) or of formula (V).

7. The composition of claim 1, comprising at least one amphoteric or zwitterionic surfactant chosen from ($C_8$-$C_{20}$) alkylbetaines, ($C_8$-$C_{20}$) alkylamido ($C_3$-$C_8$) alkylbetaines, or mixtures of two or more thereof.

8. The composition of claim 1, comprising at least one fatty alcohol chosen from linear or branched, saturated or unsaturated fatty alcohols comprising from 8 to 40 carbon atoms.

9. The composition of claim 1, comprising at least one solid fatty alcohol.

10. The composition of claim 1, further comprising at least one polysaccharide.

11. The composition of claim 10, wherein the total amount of polysaccharides ranges from 0.01% to 20% by weight, relative to the total weight of the composition.

12. The composition of claim 1, further comprising at least one silicone.

13. The composition of claim 12, wherein the total amount of silicones ranges from 0.01% to 30% by weight, relative to the total weight of the composition.

14. The composition of claim 1, further comprising at least one basifying agent.

15. A method for dyeing keratin fibers comprising applying to the keratin fibers a composition comprising:

(a) at least one cationic direct dye of formula (I):

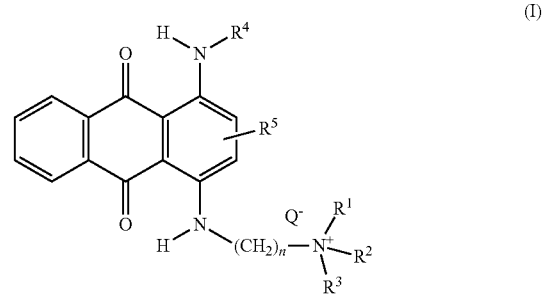

wherein:

$R^1$, $R^2$ and $R^3$ are independently chosen from a hydrogen atom or an optionally substituted ($C_1$-$C_8$) alkyl group;

$R^4$ represents a hydrogen atom or an optionally substituted ($C_1$-$C_8$) alkyl group;

$R^5$ represents a hydrogen atom, an optionally substituted ($C_1$-$C_8$) alkyl group, an optionally substituted ($C_1$-$C_8$) alkylene group, a halogen, a hydroxyl group, or a ($C_1$-$C_8$) alkoxy group;

n represents a number between 1 and 8; and $Q^-$ represents an organic or mineral anionic counterion, (b) at least one cationic surfactant, wherein the total amount of cationic surfactants ranges from 0.1% to 15%, (c) at least one amphoteric or zwitterionic surfactant, where the total amount of amphoteric and zwitterionic surfactants ranges from 0.1% to 20%, and (d) at least one fatty alcohol, wherein all amounts are by weight, relative to the total weight of the composition.

16. The method of claim 15, wherein the total amount of cationic direct dyes of formula (I) ranges from 0.01% to 15% by weight, relative to the total weight of the composition.

17. The method of claim 15, wherein the total amount of cationic surfactants ranges from 0.1% to 15% by weight, relative to the total weight of the composition.

18. The method of claim 15, wherein the total amount of amphoteric or zwitterionic surfactants ranges from 0.1% to 20% by weight, relative to the total weight of the composition.

* * * * *